(12) United States Patent
Steele et al.

(10) Patent No.: US 7,068,050 B2
(45) Date of Patent: Jun. 27, 2006

(54) MOISTURE AND DENSITY DETECTOR (MDD)

(75) Inventors: Philip H. Steele, Starkville, MS (US); Jerome E. Cooper, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 10/893,494

(22) Filed: Jul. 19, 2004

(65) Prior Publication Data

US 2005/0040832 A1 Feb. 24, 2005

Related U.S. Application Data

(63) Continuation-in-part of application No. 10/061,374, filed on Feb. 4, 2002, now Pat. No. 6,784,671.

(51) Int. Cl.
G01R 27/32 (2006.01)
G01R 27/26 (2006.01)

(52) U.S. Cl. ........................................ 324/640; 324/683

(58) Field of Classification Search ................ 324/640, 324/650, 665, 689, 683
See application file for complete search history.

(56) References Cited

U.S. PATENT DOCUMENTS

| | | | | |
|---|---|---|---|---|
| 3,430,357 A | | 3/1969 | Perry | 34/403 |
| 3,600,676 A | | 8/1971 | Ludwig et al. | 324/668 |
| 4,259,633 A | | 3/1981 | Rosenau | 324/694 |
| 4,580,233 A | | 4/1986 | Parker et al. | 73/73 |
| 4,600,692 A | | 7/1986 | Wood et al. | 435/108 |
| 4,616,425 A | | 10/1986 | Burns | 34/389 |
| 4,674,325 A | | 6/1987 | Kiyobe et al. | 73/73 |
| 4,727,311 A | | 2/1988 | Walker | 324/640 |
| 4,845,421 A | * | 7/1989 | Howarth et al. | 324/688 |
| 4,941,357 A | | 7/1990 | Schajer | 73/600 |
| 5,086,279 A | | 2/1992 | Wochnowski et al. | 324/637 |
| 5,315,258 A | | 5/1994 | Jakkula et al. | 324/640 |
| 5,402,076 A | | 3/1995 | Havener et al. | 324/689 |
| 5,463,323 A | * | 10/1995 | Wakamatsu | 324/611 |
| 5,486,815 A | | 1/1996 | Wagner | 340/602 |
| 5,537,141 A | | 7/1996 | Harper et al. | 725/116 |
| 5,585,732 A | | 12/1996 | Steele et al. | 324/663 |
| 5,767,685 A | | 6/1998 | Walker | 324/640 |
| 6,114,863 A | | 9/2000 | Krahn et al. | 324/664 |
| 6,124,584 A | * | 9/2000 | Blaker et al. | 219/779 |
| 6,147,503 A | * | 11/2000 | Nelson et al. | 324/637 |
| 6,677,763 B1 | * | 1/2004 | Geisel | 324/640 |
| 6,691,563 B1 | * | 2/2004 | Trabelsi et al. | 73/73 |

(Continued)

OTHER PUBLICATIONS

Kaestner, et al., "Microwave Polarimetry Based Wood Scanning", School of Information Science, Computer and Electrical Engineering, Halmstad University, 1999.

(Continued)

*Primary Examiner*—Anjan Deb
(74) *Attorney, Agent, or Firm*—DLA Piper Rudnick Gray Cary US LLP

(57) ABSTRACT

A Moisture and Density Detector (MDD) provides a method and apparatus to determine the moisture content and/or density, as well as presence and location of anomalies, and/or wood type of any dielectric material for various purposes. This device is very useful in detecting the moisture content of wood and wood-based materials, such as that of lumber in a dry kiln prior to, during and/or following drying. The MDD passes a radio frequency signal and/or any other signal between opposed or adjacent capacitance electrodes and measures the signal strength and phase shift of the signal. The addition of phase shift and multiple frequencies improves the accuracy of the results.

50 Claims, 7 Drawing Sheets

U.S. PATENT DOCUMENTS

| | | |
|---|---|---|
| 6,733,295 B1 | 5/2004 | Stuppy et al. .............. 434/322 |
| 6,784,671 B1 * | 8/2004 | Steele et al. ................ 324/640 |
| 2004/0133546 A1 | 7/2004 | Oni .............................. 707/1 |

OTHER PUBLICATIONS

Kabir, et al., "Temperature Dependence of the Dielectric Properties of Rubber Wood", Wood and Fiber Science, vol. 33, No. 2, pp. 233-238, 2001.

Ichijo, B., "On the New Method of Measuring Dielectric Constant and Loss Angles of Semiconductors", Jour. of Applied Physics, vol. 24, No. 3, 1953.

Hagl, et al., "Sensing Volume of Open-Ended Coaxial Probes for Dielectric Characterization of Breast Tissue at Microwave Frequencies", IEEE Transactions on Microwave Theory and Techniques, vol. 51, No. 4, 2003.

Forrer, et al., "Dielectric properties of defects on wood surfaces", Holz als Roh-und Werkstoff, vol. 56, pp. 25-29, 1998.

Athey, et al., "Measurement of Radio Frequency Permittivity of Biological Tissues with an Open-Ended Coaxial Line: Part I", IEEE Transactions on Microwave Theory and Techniques, vol. MIT-30, No. 1, 1982.

Culpepper, "High Temperature Drying", pp. 258-262, 1990.

G. I. Torgovnikov, "Dielectric Properties of Wood and Wood-Based Materials", pp. 174-181 (1993).

R. King, et al., "Measurement of Basis Weight and Moisture Content of Composite Boards Using Microwaves", Proceedings of the 8th Symposium on the NonDestructive Testing of Wood (Sep. 23-25, 1991).

P. Martin, et al., "Evaluation of Wood Characteristics: Internal Scanning of the Material by Microwaves", Wood Science Tech., vol. 21, pp. 361-371 (1987).

Jean-Francois Portala, et al., "Nondestructive Testing Techniques Applied To Wood Scanning", Industrial Metrology, vol. 2, pp. 299-307 (1992).

M. Tiitta, et al., "Development of an Electrical Impedance Spectrometer for the Analysis of Wood Transverse Moisture Gradient", Proceedings of the 12th Int'l Symposium on the NonDestructive Testing of Wood, pp. 307-316, Sep. 13-15, 2000.

N. Sobue, "Measurement of Moisture Gradient in Wood by Electrode Scanning Moisture Analysis ESMA", Proceedings of the 12th Int'l Symposium on NonDestructive Testing of Wood, pp. 301-306, Sep. 13-15, 2000.

Sina Jazayeri, et al., "Detection of Transverse Moisture Gradients in Timber by Measurements of Capacitance Using a Multiple-Electrode Arrangement", Forest Products Journal, vol. 50, No. 11/12, pp. 27-32 (2000).

Philip H. Steele, et al., "Estimating Lumber Strength With Radio Frequency Scanning", Proceedings of the 4th Int'l Conference on Image Processing and Scanning of Wood, pp. 343-348, Aug. 21-23, 2000.

Philip H. Steele, et al., "Differentiation of Knots, Distorted Grain, and Clear Wood by Radio-Frequency Scanning", Forest Products Journal, vol. 50, No. 3, pp. 58-62 (2000).

P. H. Müller, "Mechanical Stress-Grading of Structural Timber in Europe, North America and Australia", Wood Sci & Tech., vol. 2, pp. 43-72 (1968).

Jacek M. Biernacki, et al., "Economic Feasibility of Improved Strength and Stiffness Prediction of MEL and MSR Lumber", Forest Products Journal, vol. 47, No. 11/12, pp. 85-91 (1997).

* cited by examiner

505 — Radio frequency signal generated by signal generator and transmitted to amplifier

510 — Radio frequency signal amplified by amplifier and transmitted to electrodes

515 — Radio frequency signal applied to electrode 110, creating electric field sensed by electrode 120

520 — Radio frequency signal amplified by amplifier and transmitted to oscilloscope

525 — Oscilloscope measures signal strength and phase shift between the amplified signal and the signal sensed by electrode 120

530 — Computer stores and compares signal strength and phase shift to predetermined values to get estimates of MC and/or density

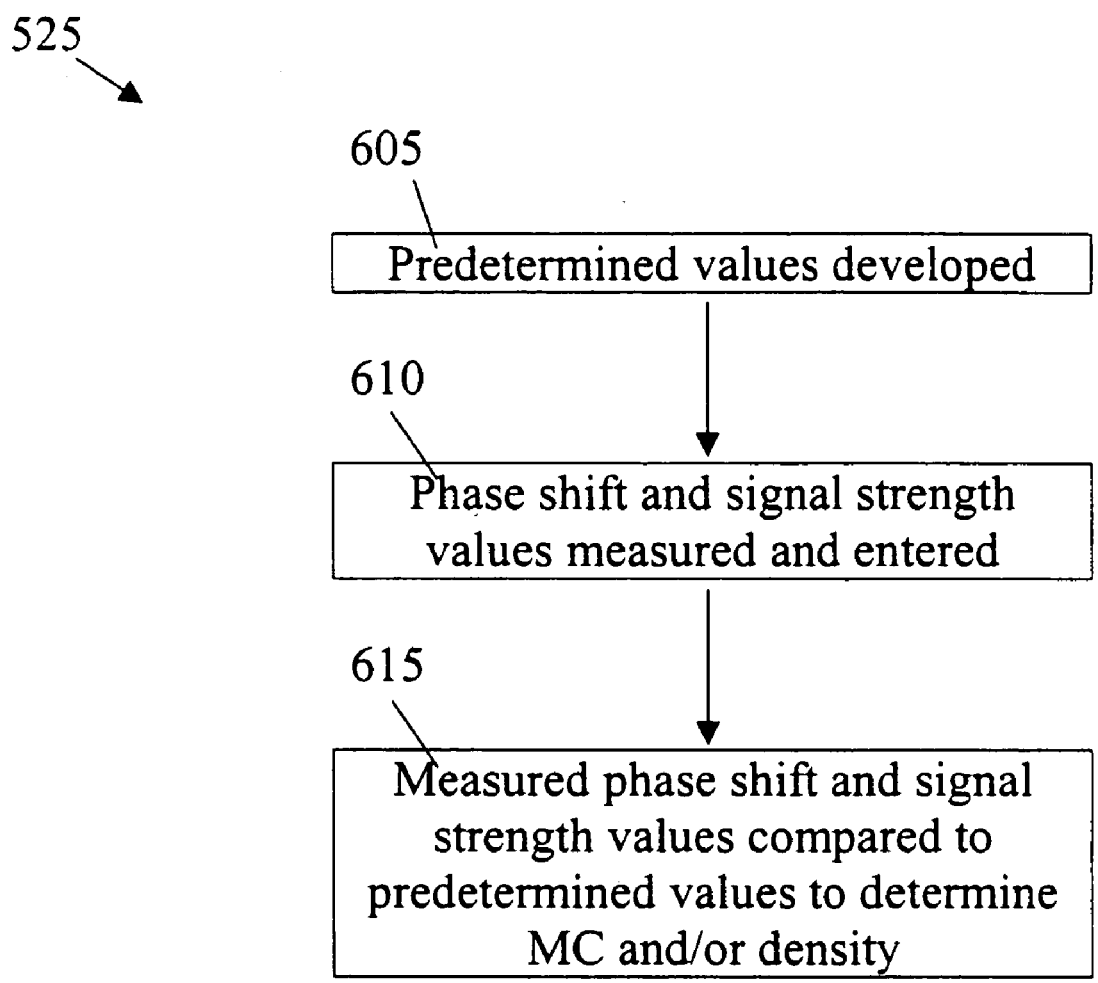

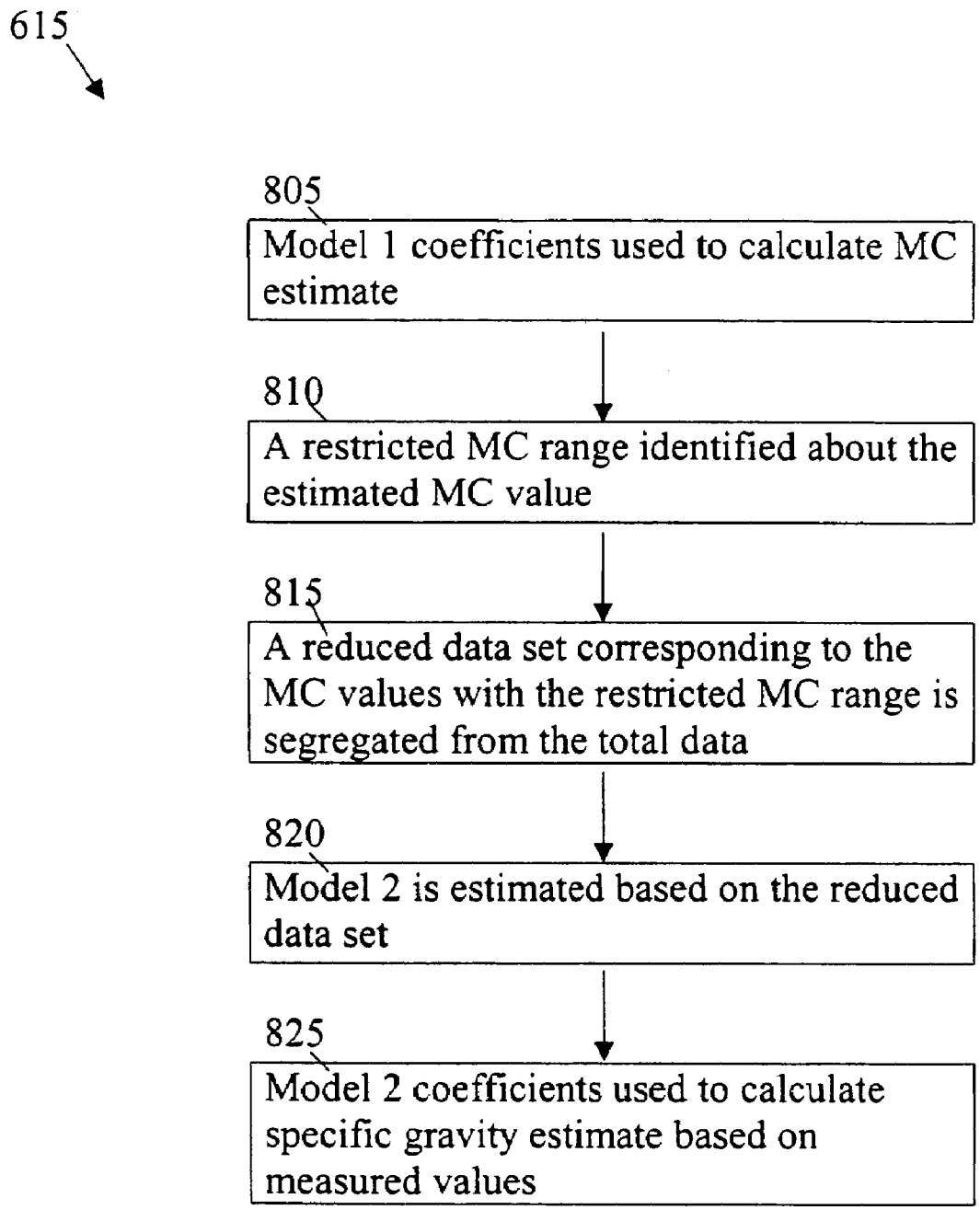

MOISTURE AND DENSITY DETECTOR (MDD)

This application is a continuation-in-part of U.S. application Ser. No. 10/061,374 filed Feb. 4, 2002, now U.S. Pat. No. 6,784,671 issued Aug. 31, 2004. The entirety of that application is incorporated herein by reference.

FEDERALLY SPONSORED DEVELOPMENT

This invention was made with U.S. Government support under grant number 2002-34158-11926 awarded by the Department of Agriculture. The U.S. Government may have certain rights in this invention.

BACKGROUND OF THE INVENTION

1. Field of the Invention

The present invention, the Moisture and Density Detector (MDD), relates to an apparatus and method for detecting the moisture content and/or density of dielectric materials.

2. Related Art

Moisture Estimation Using Radio Frequency Signals

Several devices have been developed to measure moisture in materials. These devices are based primarily on resistance and capacitance principles. Resistance is the opposition of a body or substance to a current passing through it. Capacitance is the property of a circuit element that permits it to store charge. For resistance devices, a direct current (DC) radio frequency signal is passed through a dielectric material (a material that does not conduct electricity) and the signal strength is measured as a function of the resistance of the material. This resistance measurement is then converted to a moisture content value using correction factors for temperature and species. Capacitance devices measure capacitance value or "power-loss" and estimate moisture content based on known correlation.

U.S. Pat. No. 4,259,633 to Rosenau describes a resistance moisture content estimation technique. The technique applied by Rosenau and others is limited in that it requires that metal pins be inserted into the wood sample being tested. In addition, the electrolytic polarization effects when using DC voltage can result in measurement error. Inserted-pin resistance devices are considered to provide inaccurate estimates when the wood moisture content is above the fiber saturation point of 24 to 30 percent.

U.S. Pat. No. 3,600,676 to Lugwig et al. teaches the capacitance technique whereby an alternating current (AC) radio frequency capacitance device was developed using adjacent electrodes and resonance to determine the moisture content of bulk materials (i.e., coal, chips, etc.). This device applies a range of frequencies to the dielectric material adjacent to the electrodes. The frequency with maximum signal strength is termed the resonant frequency and is a direct function of the moisture content of the dielectric material. The Lugwig et al. device determines the resonant frequency at which signal strength (amplitude) reaches a maximum. Applicant's invention also applies a range of frequencies to the dielectric material and measures the signal strength of each in terms of amplitude. However, Applicant's invention does not determine the resonant frequency but rather relates the measured amplitude of each frequency to predetermined values to determine the moisture content of the dielectric material. In addition, in contrast to Applicant's invention, the Lugwig et al. device does not use phase shift as additional information to estimate moisture content or density.

U.S. Pat. No. 4,616,425 to Burns describes an opposed electrode device based on resistance or capacitance controlled oscillator circuits. Whether based on resistance or capacitance, this device requires conversion to a frequency-dependent DC voltage. Signal strength of the DC voltage is related to predetermined voltage values for the dielectric material to allow moisture content estimation. Direct contact with the dielectric material is required. In contrast to Burns, Applicant's invention does not employ conversion from AC signal to DC signal. In addition, direct physical contact with the wood surface is possible, but not necessary. Furthermore, Burns does not use measurement of phase shift to improve the moisture content estimate. The Burns device also has no capability to estimate dielectric material density.

U.S. Pat. No. 3,430,357 to Perry discloses an opposed electrode device that measures capacitive impedance and associated moisture content in a stack of lumber in a dry kiln. The resistance between a capacitance probe inserted several courses of lumber above a ground electrode gives a measure of stack moisture content in the lumber between the electrodes. This method requires direct contact between the capacitance probe and the lumber. With the Perry device, an AC signal is converted to a DC signal prior to measurement of the signal strength as voltage. Perry differs from Applicant's invention in that Applicant directly measures the strength of the AC signal. Perry also does not employ a phase shift measurement to improve the moisture content estimate. In addition, the Perry device has no capability to estimate dielectric material density.

U.S. Pat. No. 4,580,233 to Parker et al. teaches an adjacent electrode AC moisture sensing device with two alternating frequencies that measures the imbalance in a capacitance bridge to estimate the moisture content of dielectric materials. Circuitry and methodology is incorporated to correct for potential wood temperature differences. As with the Lugwig et al., Burns, and Perry disclosures, the AC signal is converted to a DC signal prior to measurement of voltage to determine signal strength. This differs from Applicant's invention, which directly measures the strength of the AC signal. In addition, Parker et al. does not employ phase shift either to improve the moisture content estimate or to allow for estimation of dielectric material density.

U.S. Pat. No. 5,402,076 to Havener et al. recites a portable device, similar to Perry's device, that measures moisture content in a stack of lumber but with the AC radio frequency signal transmitted between adjacent electrodes. As with Perry, Applicant's invention differs because Applicant measures the phase shift and has the capability to estimate wood density.

U.S. Pat. No. 5,486,815 to Wagner discloses an in-line AC moisture meter employing opposed capacitance electrodes to sense moisture content in lumber moving between the electrodes. A single 4 MHz frequency is transmitted between electrodes and the received signal strength is measured to provide an estimate of the wood moisture content. The 4 MHz signal is applied to two pairs of electrodes with a 20-volt peak-to-peak amplitude signal applied to one pair and a 4.5 volt peak-to-peak amplitude signed to the other. The 4.5 volt signal is applied 180° out-of-phase with the higher 20-volt signal. Wagner teaches that analysis of the out-of-phase signal responses reduces the effects on the signal of electrical loading of the material. Wagner differs from Applicant's invention because Wagner does not improve the estimate of moisture content by adding phase shift information and Wagner has no described capability to estimate the dielectric material density. This device is also limited to detection of moisture content below 24 percent.

The teachings described above have employed measures of signal strength of both resistance and capacitance electrodes to estimate dielectric material moisture content. Both AC and DC devices have been developed. However, none of the described devices are reportedly accurate in measuring moisture content above the fiber saturation point of approximately 24 to 30 percent moisture content. In addition, none have employed measurement of signal phase shift to improve their estimate of moisture content. Furthermore, none report the capability of estimating the density of the dielectric material by combined analysis of amplitude and phase shift of a radio frequency signal.

U.S. Pat. No. 5,086,279 to Wochnowski discloses a means for estimating moisture content in a stream of materials by both reflecting and passing electrical energy through the stream in the form of infrared, microwave, or energy generated by a high-frequency oscillator circuit. For each of the electrical energy types, the energy is both reflected from and transmitted through the material stream. The transmitted energy from the high-frequency oscillator may be inferred to be in the same radio frequency range as Applicant's invention, although Wochnowski did not define the spectrum.

The Wochnowski moisture content estimate of the stream of materials depends on measures of signal strength and phase shift with each obtained by two methods. The two methods are to obtain a reflected signal detected by a sensor on the same side of the stream of materials and also a through signal such as is obtained by an opposed or adjacent electrode configuration. Therefore, the moisture content estimate provided by Wochnowski depends partially on the correction for the mass of the stream of materials by analysis of the "damping of oscillations" of electromagnetic waves through a first signal and a second (reflected) signal. Likewise, additional information for the moisture content analysis is obtained from the phase shift of both a through and reflected signal.

Applicant's invention differs from Wochnowski in that it requires no information on reflected energy but depends solely on its estimate of moisture content and density based on passage of the signal between the electrodes. In addition, Applicant compares phase shift and signal strength changes, caused by interaction of the radio frequency signal with the dielectric material, to predetermined values to provide the estimation of moisture content and density. Wochnowski describes no method for comparing predetermined values to correlate measured phase shift and signal strength decrease to expected values for the dielectric material at given moisture content's and densities. Applicant also provides an estimate of dielectric material density that the Wochnowski device does not provide.

In a 1993 writing, Torgovnikov discloses dielectric constants, measures of signal strength, and loss tangent values for radio frequencies from 20 to 1000 Hz. G. Torgovnikov, DIELECTRIC PROPERTIES OF WOOD AND WOOD-BASED MATERIALS 174–181 (1993). (The terms loss tangent and phase shift are both referenced herein. While these terms differ in their meaning, they are mutually direct functions with one easily derived from the other. For this reason, devices designed to provide information for one also indirectly provide the other value. In that sense these terms will be used interchangeably.) For all frequencies tested, Torgovnikov shows via plotted regressions that the rate of increase in the dielectric constant is higher for moisture content below the fiber saturation point. The plotted slopes of the regression lines also appear to have significant slope above the fiber saturation point. These plotted regression lines, however, represent the mean dielectric response for a range of wood specific gravity values.

Torgovnikov also teaches that the dielectric response is strongly influenced by the wood specific gravity. Therefore, dielectric constant information alone will not allow an accurate estimation of wood moisture content because of the confounding influence of wood density. With current methods this confounding influence can only be eliminated if a single wood density is scanned or if the density of specimens is known. Torgovnikov does not provides a method to improve moisture content estimate by including phase shift or loss tangent as a predictive variable.

Moisture Estimation Using Microwaves

Attempts have been made to measure the moisture content of materials using microwave energy. U.S. Pat. Nos. 4,727,311 and 5,767,685 to Walker teach ways to measure the moisture content of materials such as sand and coal. In these cases, two microwave frequencies are passed through a material in order to determine moisture content. The difference between the two signals assists in determining moisture content.

U.S. Pat. No. 4,674,325 to Kiyobe et al. calculates moisture content by passing material between non-contacting microwave horns. The basis weight is detected with an ionizing chamber.

U.S. Pat. No. 5,315,258 to Jakkula et al. discloses a radar system developed for measuring the moisture content of materials. There, the change in velocity of the microwaves within the material is correlated to differences in moisture content.

The Walker, Kiyobe et al., and Jakkula et al. teachings differ from Applicant's invention in that a microwave signal rather than signals in the radio frequency spectrum are utilized. Microwave devices require wave guides to transmit and receive the signals while radio frequency devices such as the Applicant's require only electrodes. These microwave devices described also do not have the capability to estimate dielectric material density.

The following disclosures describe microwave devices based on the attenuation of the microwave signal to estimate moisture content combined with information on phase shift of the microwave signal to provide wood density information:

R. King et al., *Microwave Measurement of the Complex Dielectric Tensor of Anisotropic Slab Materials*, in PROCEEDINGS OF A TECHNOLOGY AWARENESS SEMINAR (Nov. 15–16, 1987).

R. King et al., *Measurement of Basis Weight and Moisture Content of Composite Boards Using Microwaves*, in PROCEEDINGS OF THE 8TH SYMPOSIUM ON THE NONDESTRUCTIVE TESTING OF WOOD (Sep. 23–25, 1991).

P. Martin et al., *Evaluation of Wood Characteristics: Internal Scanning of the Material by Microwaves*, in 21 WOOD SCIENCE TECH. 367–371 (1987).

P. Martin et al., *Industrial Microwave Sensors for Evaluation of Wood Quality*, in FOURTH INT'L CONFERENCE ON SCANNING TECHNOLOGY IN THE WOOD INDUSTRY (1991).

J. Portala & J. Ciccotelli, *Nondestructive Testing Techniques Applied to Wood Scanning*, in 2 INDUSTRIAL METROLOGY 299–307 (1992).

King et al. (1987), King et al. (1983), Martin et al. (1987), Martin et al. (1991), and Portala et al. (1992) depend for their estimates of moisture content and density on the analysis of both attenuation and phase shift. These devices differ from applicant's device in that the microwaves are applied by horns, rather than by the electrodes utilized by Applicant's device. No electrode based radio frequency or microwave device has been disclosed that combines analysis of changes in signal amplitude and phase shift to estimate wood moisture content and density, with the exception of Wochnowski. As discussed, this device requires information on both reflected and through-material amplitude and phase shift signals to obtain estimated material moisture content.

Radio Frequency Moisture Gradient Estimation

An impedance detector disclosed by Tiitta et al. measures the moisture gradient in wood. M. Tiitta et al., *Development of an Electrical Impedance Spectrometer for the Analysis of Wood Transverse Moisture Gradient*, in PROCEEDINGS OF THE 12$^{TH}$ INT'L SYMPOSIUM ON NONDESTRUCTIVE TESTING OF WOOD (Sep. 13–15, 2000). Electrodes contained in a probe are placed on the wood surface. One electrode transmits an electrical signal at frequencies below 5 MHz, and the second receives the signal. A variable electric field is developed between the electrodes. Analysis of the behavior of impedance, or signal strength, for the various frequencies transmitted through the wood allows estimation of the moisture gradient within the wood. This device was developed to sense the moisture gradient in logs.

Writings by Sobue and Jazayeri et al. have demonstrated a method to sense the moisture gradient in wood by what Sobue termed Electrode Scanning Moisture Analysis (ESMA). N. Sobue, *Measurement of Moisture Gradient in Wood by Electrode Scanning Moisture Analysis ESMA*, in PROCEEDINGS OF THE 12$^{TH}$ INT'L SYMPOSIUM ON NONDESTRUCTIVE TESTING OF WOOD (Sep. 13–15, 2000); S. Jazayeri & K. Ahmet, *Detection of Transverse Moisture Gradients in Timber by Measurements of Capacitance Using a Multiple-Electrode Arrangement*, 50 FOREST PROD. J. 27–32 (2000). ESMA determines moisture content at various depths through wood thickness by manipulating the distance between adjacent electrodes on a single wood surface between 0.43 in. (11 mm) and 1.97 in (50 mm), shown in FIG. 1. Examination of the capacitance changes developed by manipulation of electrode distance allows computation of wood moisture gradient at various depths through wood thickness. Sobue's method allowed measurement of moisture content in wood up to 120 percent. Sobue and Jazayeri et al., however, demonstrated that this method would work for only a single wood density in which moisture content levels were manipulated.

The Tiitta et al., Sobue, and Jazayeri et al. devices are adjacent electrode impedance devices that are designed to estimate moisture gradient rather than average moisture content. The ability to estimate wood density as well as moisture gradient was not demonstrated by this device. By contrast, Applicant's invention is an opposed or adjacent plate capacitance device that senses mean moisture content and may also provide an estimate of wood density. Neither the Tiitta et al., Sobue, or Jazayeri et al. devices employ phase shift to improve their estimate of moisture content or to provide an estimate of wood density.

U.S. Pat. No. 5,585,732 to Steele et al. and two writings by Steele et al. have disclosed a method for detecting density differences in scanned lumber by a radio frequency method with opposed electrodes. P. Steele & J. Cooper, *Estimating Strength Properties of Lumber with Radio Frequency Scanning*, in PROC. OF THE 4TH INT'L CONFERENCE ON IMAGE PROCESSING AND SCANNING OF WOOD (Aug. 21–23, 2000); P. Steele et al., *Differentiation of Knots, Distorted Grain, and Clear Wood by Radio-Frequency Scanning*, 50 FOREST PROD. J. 58–62 (2000). To date, only detection of knots and voids has been described as being detected. The application of phase shift or loss tangent to assist in more accurately estimating dielectric material moisture content or estimating density has not been disclosed for this or any other radio frequency device.

The disclosures by Steele et al. employed dielectric properties and wood density in the estimation of wood strength by radio frequency capacitance employing a variation of the Steele et al. device. However, the Steele et al. method depended on prior knowledge of wood moisture content with statistical correction for the known moisture content differences. Validation of this method showed an $R^2$ value of 0.67 between attenuated dielectric signal and lumber modulus of rupture. Only a single radio frequency signal attenuation measurement to provide specific gravity estimates was employed. Applicant's invention, by contrast, may employ single or multiple radio frequency signals to obtain dielectric constant. The Steele et al. method did not measure phase shift to improve the estimate of wood density.

Wood Strength Estimation Based on Density Detection

The amount of lumber graded by machine stress rating (MSR) has continued to increase since the development of the technology in the early 1960's. This growth has been driven by the significant premium in value for MSR versus visually graded lumber in certain lumber grades. MSR graded lumber is mechanically flexed to obtain a flatwise modulus of elasticity. In a 1968 writing, Muller teaches a method of estimating lumber grade based on the known relationship between modulus of elasticity and modulus of rupture combined with additional information from visual inspection of the lumber. P. Muller, *Mechanical Stress-Grading of Structural Timber in Europe, North America and Australia*, 2 WOOD SCI. & TECH. 43–72 (1968). In addition, in 1997 Biernacki et al. indicated a significant potential for increased lumber value from improved accuracy in lumber grading. $R^2$ values based on relating modulus of elasticity to modulus of rupture are species dependent but are approximately 0.50. J. Biernacki et al., *Economic Feasibility of Improved Strength and Stiffness Prediction of MEL and MSR Lumber*, 47 FOREST PROD. J. 85–91 (1997).

U.S. Pat. No. 4,941,357 to Schajer discloses an alternative to MSR lumber grading that is a system that estimates lumber strength based on x-ray through-lumber-thickness scanning. By this method the lumber strength is estimated by assigning a clear wood strength value with deductions based on knot presence indicated by specific gravity scans. Lumber strength estimations based on x-ray scanning is reported to be higher than MSR estimates with $R^2$ values ranging between 0.68 and 0.78 for southern yellow pine lumber.

Applicant's invention has potential as an MSR device capable of predicting clear wood density. In such use, Applicant's invention will require a knot detection system such as a digital camera, ultrasound, radio frequency, infrared, etc. MSR lumber grading requires information on knot size and location in addition to density of clear wood. Also required will be techniques and software to correct for knot influence on lumber strength.

Additional Information

Researchers have employed microwave horns and open-ended coaxial cables to detect the moisture content, density, and characteristics of biological tissue including wood. Some devices such as Walker (U.S. Pat. Nos. 4,727,311 and 5,767,685), Kiyobe et al. (U.S. Pat. No. 4,674,325) utilize horns to direct microwaves through material and determine the moisture content based on the microwave attenuation. Jakkula et al. (U.S. Pat. No. 4,674,325) disclose a radar system that passes microwaves through materials whereby moisture content is correlated to changes in microwave velocity. Applicant's invention, by contrast, utilizes microwave signals applied by electrodes rather than horns. Also, in addition to signal attenuation, phase shift information is utilized by Applicant to allow more accurate estimation of dielectric material moisture content and density.

Other researchers, listed below, have applied microwaves to wood with microwave horns. They have measured both the attenuation and phase shift of the microwave signal and have utilized the known relationship of these signals to estimate both wood density and moisture content. Applicant's invention is similar to these devices and methods described in that the combined information on signal attenuation and phase shift is utilized to estimate wood moisture content and density. However, Applicant's device employs electrodes rather than horns to apply and receive the microwaves.

R. King et al., *Microwave Measurement of the Complex Dielectric Tensor of Anisotropic Slab Materials,* in PROCEEDINGS OF A TECHNOLOGY AWARENESS SEMINAR (Nov. 15–16, 1987).

R. King et al., *Measurement of Basis Weight and Moisture Content of Composite Boards Using Microwaves,* in PROCEEDINGS OF THE 8TH SYMPOSIUM ON THE NONDESTRUCTIVE TESTING OF WOOD (Sep. 23–25, 1991).

P. Martin et al., *Evaluation of Wood Characteristics: Internal Scanning of the Material by Microwaves,* in 21 WOOD SCIENCE TECH. 367–371 (1987).

P. Martin et al., *Industrial Microwave Sensors for Evaluation of Wood Quality,* in FOURTH INT'L CONFERENCE ON SCANNING TECHNOLOGY IN THE WOOD INDUSTRY (1991).

J. Portala & J. Ciccotelli, *Nondestructive Testing Techniques Applied to Wood Scanning,* in 2 INDUSTRIAL METROLOGY 299–307 (1992).

Wochnowski (U.S. Pat. No. 5,086,279) has disclosed application of electromagnetic waves and simultaneous measurement of their transmission through, and reflectance from, materials. He utilized this information to estimate moisture content and density of the materials. Means of application and frequency was not specified. Applicant's invention does not utilize electromagnetic wave reflectance information to arrive at an estimate of dielectric material moisture content and density.

Numerous researchers, such as those listed below, have employed open-ended coaxial cables applying microwaves to measure dielectric properties of biological materials, including wood. Applicant's application of microwave signals is achieved with electrodes rather than with open-ended coaxial cables.

Atheny, T. W., M. A. Stuchly & S. S. Stuchly, 1982. *Measurement of RF Permittivity of Biological Tissues with an Open-Ended Coaxial Line.* IEEE. TRANS. MTT. 30:82–86.

Hagl, D. M., D. Popovic, S. C. Haguess, J. H. Brooke, & M. Okoniewski. 2003. *Sensing Volume of Open-Ended Coaxial Probes for Dielectric Characterization of Breast Tissue at Microwave Frequencies.* IEEE. TRANS. MTT. 51(4):1194–1206.

Kabir, M. F., W. M. Daud, K. B. Khalid & H. A. A. Sidek. 2001. *Temperature Dependence of the Dielectric Properties of Rubber Wood.* WOOD AND FIBER SCIENCE. 33(2):233–238.

Steele & Kumar (U.S. Pat. No. 5,585,732) describe a radio frequency knot and void detection device utilizing opposed electrodes to detect knots and voids.

Forrer & Funck have also utilized a variation of a device disclosed by Ichijo in 1953. The Ichijo device is a resonant guard electrode design for sensing dielectric properties of dielectric materials. Opposed electrodes are placed in direct contact with surface of the dielectric material. Forrer & Funck applied their variant of the device to detect wood types such as knots, clear wood, pitch streaks, pitch pockets, voids and blue stain. Moderate success in correlating these defect types with attenuation and phase shift were successful but considerable overlap was found among these measures depending on the wood types. Frequency applied was in the radio frequency range between 1.4 and 20 MHz and was, therefore, restricted to the radio frequency range. This work by Forrer & Funck and by Ichijo was reported in the following papers:

Forrer, J. & J. Funck. 1998. *Dielectric Properties of Defects on Wood Surfaces.* HOLZ ALS ROH-UND WERKSTOFF. 56(1):25–29.

Ichijo, B. 1953. *On the New Method of Measuring Dielectric Constant and Loss Angles of Semiconductors.* J. APPL. PHYS. 24(3):307–311.

Applicant's invention differs from the Forrer & Funck device in several important ways, including but not limited to the following. One important difference is that the Forrer & Funck device utilizes a resonance-based method and circuit to determine the dielectric constant and loss tangent of the wood types. The resonance device requires relatively complex circuitry comprising multiple resistors and capacitors. Also, the dielectric material scanned must be physically manipulated multiple times following calibration steps to determine the dielectric constant and loss tangent of the dielectric material. This method is obviously not suited to scanning wood to detect wood types for industrial purposes. Applicant's invention, by contrast, applies a discrete frequency and utilizes measurement devices to determine attenuation (related to dielectric constant) and phase shift (related to loss tangent). Thus, applicants method is adaptable to industrial scanning speeds.

Forrer & Funck also demonstrate no method for identifying wood types from the dielectric constant and loss tangent data. Neither regression equations nor threshold values based on predetermined values were utilized. Rather, dielectric constant values were merely plotted versus loss tangent values to indicate a graphical relationship and distribution of response to wood types. Thus, applicants method is adaptable to industrial scanning speeds.

Researchers, listed below, have reported on a method and device to detect knots and other anomalies in logs by analysis of depolarized reflected microwaves transmitted from a microwave horn. Knots and log pith were successfully visualized. This device differs from Applicant's method in that microwaves are applied by Applicant by electrodes rather than horns.

Kaestner, A. P. and L. B. Baath. 2000. *Microwave Polarimetry Based Wood Scanning.* PROC. OF THE 12th INT. SYMPOSIUM ON NONDESTRUCTIVE TESTING OF WOOD. University of Western Hungary, September 13–15. Sopron, Hungary. 474 p.

The patent titled "Determining the Dielectric Properties of Wood," (DDPW), numbered PCT/US96/03604 with International Publication Number WO 96/28741 and International Publication Date Sep. 19, 1996, invented by Venter & Viljoen, provides no method for determining the density of the wood between the electrodes.

The patent titled "Dielectric Sensor Apparatus", numbered U.S. Pat. No. 5,654,643, invented by Bechtel et al. senses dielectric materials utilizing cancellation of capacative coupling.

BACKGROUND OF THE TECHNOLOGY

After logs are milled and lumber is created, the lumber is usually dried. Softwood lumber is a challenge to dry, and hardwood lumber is even more difficult. A key difference between hardwood and softwood lumber drying is the initial moisture content at the start of kiln drying. Wood moisture content may vary from 0% to a "green" measure. A green measure of moisture content may be as high or higher than 200 percent. Softwood lumber is dried green immediately after it is sawn. The average initial moisture content of softwood lumber is often greater than one-hundred percent, based on oven-dry weight. Typically, hardwood lumber has a significantly lower initial moisture content than softwood lumber. When dried directly from the saw, hardwood lumber is typically between sixty and eighty percent moisture content while softwood lumber frequently exceeds 100 percent moisture content. Often, hardwood lumber is air dried to reduce its initial moisture content to approximately 25 percent before being dried. In contrast, softwood lumber is often dried green at, or above, 100 percent moisture content.

Lumber in dry kilns can be monitored for drying rate and for final moisture content at the drying schedule endpoint by either moisture content schedules or time-based schedules. Moisture content schedules monitor the rate of drying by periodically weighing previously cut short lumber samples during drying to measure the moisture content. Time-based schedules do not require lumber samples, but instead assume that the rate of drying is correlated with kiln conditions and the time over which the conditions are applied to the lumber. Time-based schedules are widely used in the drying of softwood lumber because softwood lumber is less susceptible to drying degrade caused by drying the wood at an improper rate. However, failure to control the drying rate when applying pre-set time schedules is responsible for considerable lumber degrade during drying. In order for time-based schedules to work well, each lumber load placed in the kiln must have approximately the same initial moisture content, the same permeability, and kiln conditions must be identical from charge to charge. These requirements are not always satisfied and lumber drying degrade often occurs.

For most hardwood species, moisture content schedules must be used to prevent dramatic value losses from drying degrade. Traditional moisture content schedules require the kiln operator to control the drying rate by monitoring the moisture content of several kiln samples. These samples are two to three-feet long and are dried with the kiln charge of lumber. Prior to the start of drying, a moisture content section is cut from each kiln sample. This section is rapidly oven dried to determine the initial moisture content of the wood going into the kiln. This initial moisture content value is used in conjunction with the sample weight to determine the samples' moisture content throughout the drying run. This continual monitoring allows control of the kiln conditions, and the lumber's drying rate is based on the average sample moisture content.

The process of monitoring kiln samples requires kiln operators to repeatedly enter the dry kiln to remove kiln samples for monitoring by weighing. Following weighing, the kiln samples must be returned immediately to the dry kiln. Softwood lumber of nominal two-inch thickness is dried at high temperatures from green wood and the drying process usually requires less than 24 hours. In the case of air-dried hardwoods of four-quarter-inch thickness, the approximate drying time is between four and eleven days.

Monitoring moisture content samples over a short-time interval (24 hours or less) makes it difficult for operators to apply moisture content schedules for softwoods without additional technology. For both hardwood and softwood, kiln drying technological developments in recent years have produced several new methods to estimate the moisture content drying rate and drying end point. Reports on the effectiveness of these systems has been provided by Culpepper. L. Culpepper, HIGH TEMPERATURE DRYING 258–262 (1990).

One method for estimating the moisture content drying rate is temperature drop-across-the-load monitoring, which monitors the temperature of the air flowing across the drying lumber. The air temperature decrease from lumber entry to lumber exit is closely correlated to the wood moisture content for moisture content below the fiber saturation point, but the method is inaccurate above the fiber saturation point.

Another method for estimating the moisture content drying rate uses electrical resistance devices and employs pairs of pins inserted into holes drilled into the lumber. The distance between the pins is limited (1" to 2") to allow an applied low voltage to flow between the two pins. The resulting resistance is measured and correlated to wood moisture content. The resistance devices accurately predict the moisture content below the fiber saturation point, but inaccurately predict the wood moisture content above the fiber saturation point.

An additional method uses an electrical capacitance method to measure the capacitance between plates inserted in the stack and kiln rails which are grounded. This method has been shown to provide a moisture content measurement that is often not accurate.

Weight-based systems are another method used to measure wood moisture content. These systems measure the total weight of kiln lumber during drying. This allows close monitoring of the drying rate. These systems are reportedly accurate, but problems with sensor durability in the harsh kiln environment and the relatively high cost of using weight-based systems has limited their widespread adoption.

A more recent weight-based system not reviewed by Culpepper monitors the weight of a kiln sample suspended in the kiln plenum, which is the space around the lumber. This system is reportedly effective but the relatively high cost of the system has limited its adoption.

As summarized above, systems that measure moisture content during kiln drying to monitor drying rate and drying end point are available. However, these systems are relatively expensive and not always effective at monitoring wood moisture content. There exists a need for improved methods to monitor drying rate and drying end point.

The ability to estimate wood density is also needed in the wood processing industry. The term density as employed herein refers to the oven-dry specific gravity of a dielectric material. A dielectric material is a material that does not conduct electricity. For hygroscopic materials that readily absorb water, such as wood, the specific gravity differs from the density when the material moisture content is greater than zero. Wood density varies significantly, both between and within species. In addition to the need to detect the moisture content and/or density of lumber, there exists a need to detect the moisture content and/or density of wood particles and flakes, wood composite products, and other dielectric materials (such as rubber, plastics, and foods).

Detection of moisture content and/or density of wood provides a means to characterize wood with regard to anomalies and wood types. Detection of knots and voids or identification of juvenile, compression, wetwood or other wood types will allow a means of sorting wood into quality or utilization classes.

SUMMARY OF THE INVENTION

The present invention, a MDD can provide a method and apparatus to determine an unknown moisture content, density, anomaly, wood type, material type and/or other unknown characteristic of any dielectric material for various purposes. Examples of dielectric materials that can be used with the MDD include, but are not limited to, wood-based materials, wood composites, agricultural and food products, plastic, and rubber.

In one embodiment, the present invention can be used to detect an anomaly and/or a wood type of a dielectric material, such as lumber. Lumber is scanned and an array of values is captured representing the attenuation and/or phase shift response of the signal to the nature of the wood material. This array of information provides predetermined values from the dielectric material regarding the attenuation and/or phase shift signal response to variations in moisture content, density, anomaly presence or wood type. These predetermined values allow development of regression equations, threshold values or any other means for estimating moisture content or density differences, anomalies, wood type, material type or other dielectric material characteristics. For example, Applicants have observed that phase shift decreases significantly when the applied signal interacts with the juvenile wood type in green wood while attenuation changes very little. This response, if unique to juvenile wood, will allow positive identification of juvenile wood.

Regression equation values are values derived using a statistical technique predicting the behavior of dependent variables based on known variables which we term herein as predetermined values. For example, in one embodiment of the invention, all possible moisture content and density values are recorded, and a regression equation is used to predetermine phase shift and attenuation values for all expected moistures and densities. The regression equation is then suitable for estimating the unknown moisture content, density values, or any other characteristic of the dielectric material.

Likewise, threshold values can be developed from predetermined values to determine the expected attenuation and phase shift response for moisture content, anomaly, wood types, and/or other dielectric material characteristics. In one embodiment the threshold values may be developed prior to scanning of the dielectric material. In a second embodiment the threshold values may be determined during processing of the dielectric material. Using lumber as an example, the relative response of signals to moisture content, anomalies and wood type may differ if there is a moisture content difference between pieces of lumber being scanned. Therefore the threshold values for attenuation and phase shift may differ between each scanned piece of lumber.

Therefore, threshold values may need to be computed based on predetermined knowledge of signal response during processing. In this embodiment the lumber is scanned and an array of values is captured representing the attenuation and/or phase shift of the signal response caused by the wood types or anomalies present. The array of data is gathered and threshold values are calculated based on the relative responses analyzed in the light of previous knowledge (obtained from predetermined values) as to signal reaction to anomalies and/or wood types. The array data is then analyzed to determine the presence of anomalies and wood types based on the computed threshold values calculated from the data. While this example was based on threshold values to identify anomalies or wood types, the previously described regression or any other method of identifying anomalies based on differential signal response of attenuation and/or phase shift may be employed for this purpose.

Although the MDD can be used for any dielectric material, it is very useful in detecting the moisture content of wood and wood-based materials. In particular, the MDD can be used to detect the moisture content and/or density of lumber in a dry kiln prior to, during, and/or following drying.

In addition, the MDD can detect the moisture content and/or density for the purpose of assigning lumber or veneer strength grades. The MDD can also detect moisture content and/or density of lumber, logs, poles, flakes, particles, composite panels, or any other form of solid wood product for any other purpose.

The MDD can also be used to monitor green wood moisture content prior to and following drying. In this case lumber, veneer, flakes, particles, etc., can be monitored and subsequently sorted on the basis of moisture content. Green sorting of lumber by weight is commonly done at sawmills that wish to maximize kiln capacity. Lumber with different moisture contents can be dried separately allowing lumber with lower moisture content to be dried more rapidly. Dry sorting to detect wet wood both between and within individual pieces of lumber to identify those pieces requiring further drying is also a potential application.

In addition, the MDD can be used as a machine stress rating (MSR) device by which lumber strength is assessed based on density.

The above and other objects and advantages of the present invention will become more apparent from a reading of the following detailed description of the invention in conjunction with the drawings and appended claims.

BRIEF DESCRIPTION OF THE DRAWINGS

FIG. 5 is a flowchart illustrating an exemplary process for determining the moisture content and/or density of any dielectric material.

FIG. 6 is a flowchart illustrating an exemplary process for step 525 of FIG. 5.

FIG. 8 is a flowchart illustrating an exemplary process for step 615 of FIG. 6.

DETAILED DESCRIPTION OF THE INVENTION

The present invention is directed to an apparatus and method for estimating moisture content and/or density of dielectric materials. The present invention can sense the dielectric response of a radio frequency signal or any other signal passed through the dielectric material. A radio frequency signal or other signal can be passed between opposed or adjacent capacitance electrodes and can measure the signal strength and phase shift of the signal. The addition of phase shift and multiple frequencies can improve the accuracy of the results of this type of device for multiple layer scanning.

Although the MDD can be used for any dielectric material, it is very useful in detecting the moisture content and/or density of wood and wood-based materials. In particular, the MDD can be used to detect the moisture content and/or density of lumber in a dry kiln prior to, during and/or following drying.

Figure 1:
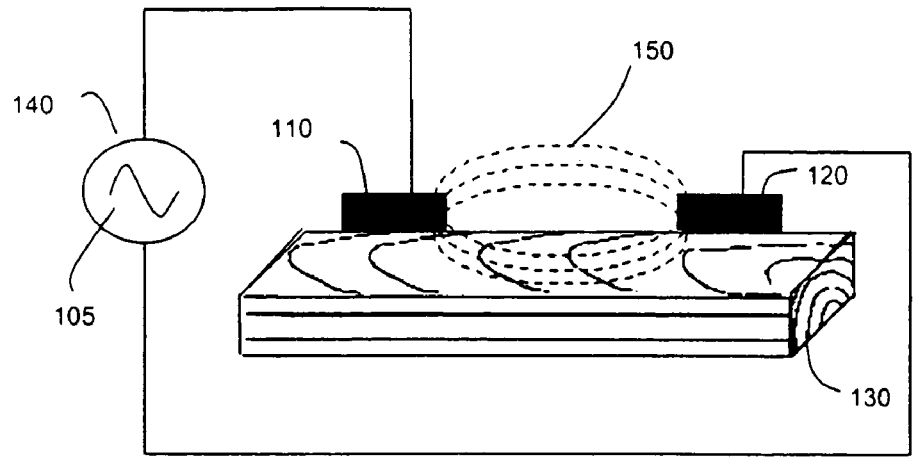
FIG. 1 displays an exemplary embodiment of an adjacent electrode radio-frequency device.

FIG. 1 displays an exemplary embodiment of an adjacent electrode radio-frequency device. The terms adjacent electrode and opposed electrode denote the relative position of electrodes with respect to each other. In an alternative embodiment, the electrodes may also be comprised of one or more adjacent pairs of electrodes or opposed and adjacent pairs of electrodes may be combined in the same device. Therefore, electrode pairs may be oriented at any angle best suited for scanning the dielectric material.

The electrodes 110 and 120 are used for transmitting and receiving the radio frequency signal or other signal 105 through the dielectric material. The electrodes 110 and 120 may be of any shape and size and constructed of any electrically conductive material. Other materials may be incorporated into the electrodes 110 and 120. The electrodes 110 and 120 may be positioned at a distance from the dielectric material surface or may be in direct contact. The electrodes 110 and 120 may be comprised of brushes, rolling transducers, or be of any other type. Capacitance, and therefore signal strength, is increased as plate size and material conductivity increases.

In one exemplary embodiment, the MDD can use an electrode shape that is rectangular and 3.0-inch by 9.0-inch in dimension. A long axis of plate is aligned with a long axis of lumber. The plates can be positioned 0.250 inch from a lumber surface, but direct contact is also feasible for stationary wood scanning. The actual distance that the electrodes 110 and 120 are positioned from the surface of the dielectric material may vary depending on the signal strength, frequency applied, or need of the specific application.

In another exemplary embodiment, the MDD can use an electrode shape of steel brushes applied to a wood surface. Brushes can be applied in both the adjacent and opposed method.

In an alternate exemplary embodiment, the transmitting electrode 110 may temporarily become a receiving electrode 120 and the receiving electrode 120 can become a transmitting electrode 110. This alteration in roles would be achieved by software or electronic switching, and would be obvious to one experienced in the art. In yet another exemplary embodiment, the MDD can measure the moisture content and/or density of each face of a dielectric material. In the case of wood, for example, compression wood, wet wood, and juvenile wood all differ in moisture content and density from normal wood. A piece of lumber may be composed of normal wood on one face and compression wood, wet wood or juvenile wood on another. Application of adjacent electrodes on each board face would allow comparison of differences in moisture content and/or density between the two faces. This would allow determination of the presence of these wood types on a single lumber face.

FIG. 1 shows an adjacent electrode configuration in which both electrodes 110 and 120 are positioned on the same side of the wood surface 130. A radio frequency signal or other signal generating device 140 generates a radio frequency signal or other signal 105 that is applied to the transmitting electrode 110 and sensed by the receiving electrode 120 through an electric field 150. The radio frequency signal or other signal 105 penetrates the wood 130 on the side on which the electrodes 110 and 120 are positioned.

Figure 2:
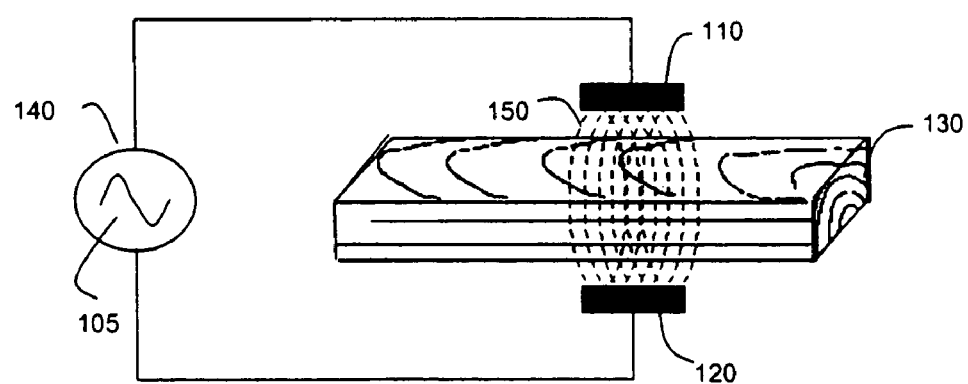
FIG. 2 displays an exemplary embodiment of a parallel opposed electrode device.

FIG. 2 displays an exemplary embodiment of a parallel opposed electrode device. Electrodes 110 and 120 are positioned on opposite sides of the wood material 130. A radio frequency signal or other signal generating device 140 generates a radio frequency signal or other signal 105 that is applied to the transmitting electrode 110 and transmitted through the wood material 130 through the electric field 150. The radio frequency signal or other signal 105 penetrates through the wood material from one side to the other.

Figure 3:
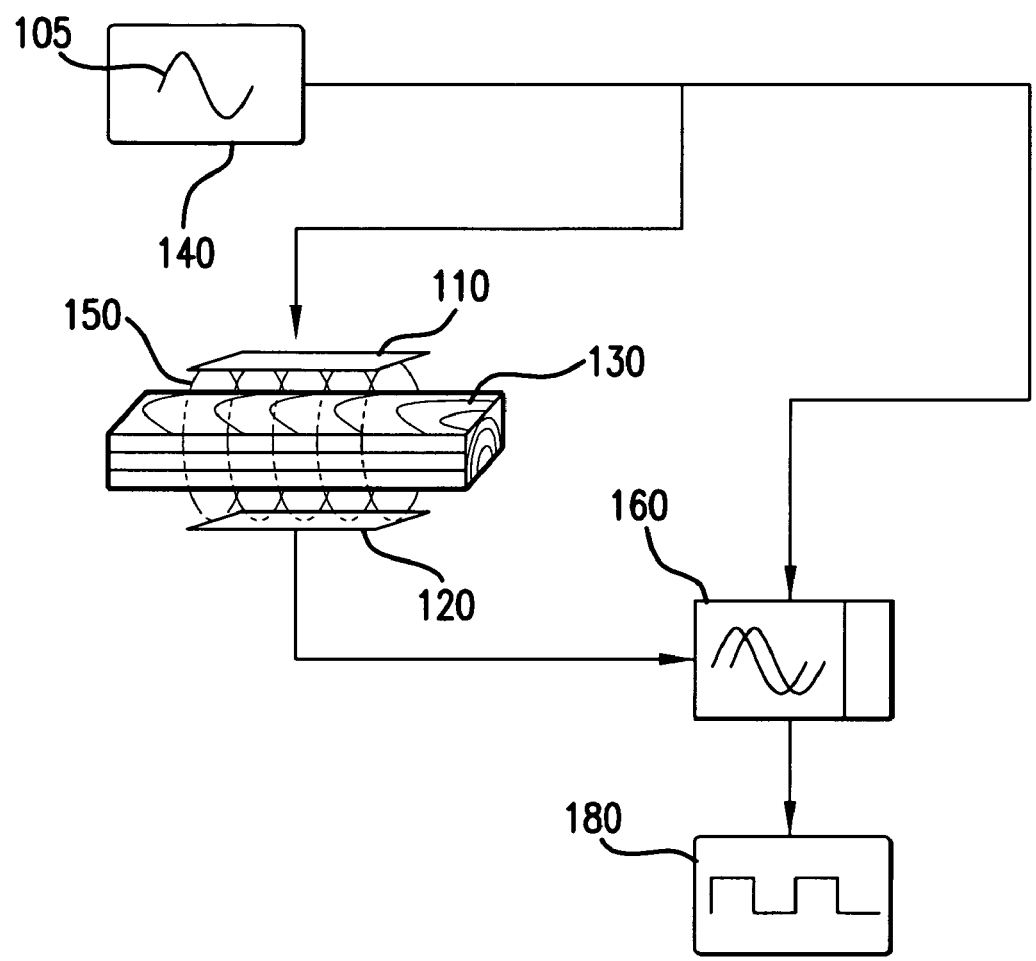
FIG. 3 displays a diagram of an exemplary embodiment of the present invention, a MDD.

FIG. 3 displays a diagram of an exemplary embodiment of the present invention, a MDD. FIG. 3 displays the architecture of the present invention. A radio frequency signal or other signal 105 moves through this apparatus. The apparatus is a moisture content and/or density detector comprised of: a means for generating a radio frequency signal or other signal 140; one or more pairs of electrodes 110 and 120; an electric field 150 passing through the wood material; a means for measuring the radio frequency signal or other signal 160; and a means for comparing the measured radio frequency signal or other signal to predetermined values 180.

The radio frequency signal or other signal 105 can be one or multiple radio frequency signals or other signals 105. Knot presence in lumber may increase or decrease the strength of the dielectric signal or other signal depending on the knot characteristics relative to the clear wood. Likewise, a void in the lumber will decrease the strength of the signal. For the purpose of kiln monitoring an operator can easily avoid placement of plates over knots or voids. For lumber sorters in which lumber is passed at speed past electrodes a method to eliminate knots from the data may be preferable. For this purpose, knot and void detection equipment such as a digital camera, ultrasound, x-ray, other radio frequency device, or any other device may be employed.

The means 160 for measuring the signal strength and phase shift of the radio frequency signal or other signal 105 measures the signal strength and phase shift caused by the interaction of the radio frequency signal or other signal 105 with the dielectric material.

The means for comparing the measured radio frequency signal or other signal to predetermined values 180 compares the signal strength and the phase shift of the radio frequency signal or other signal 105 to predetermined values to get an estimate of the moisture content and/or density.

Figure 4:
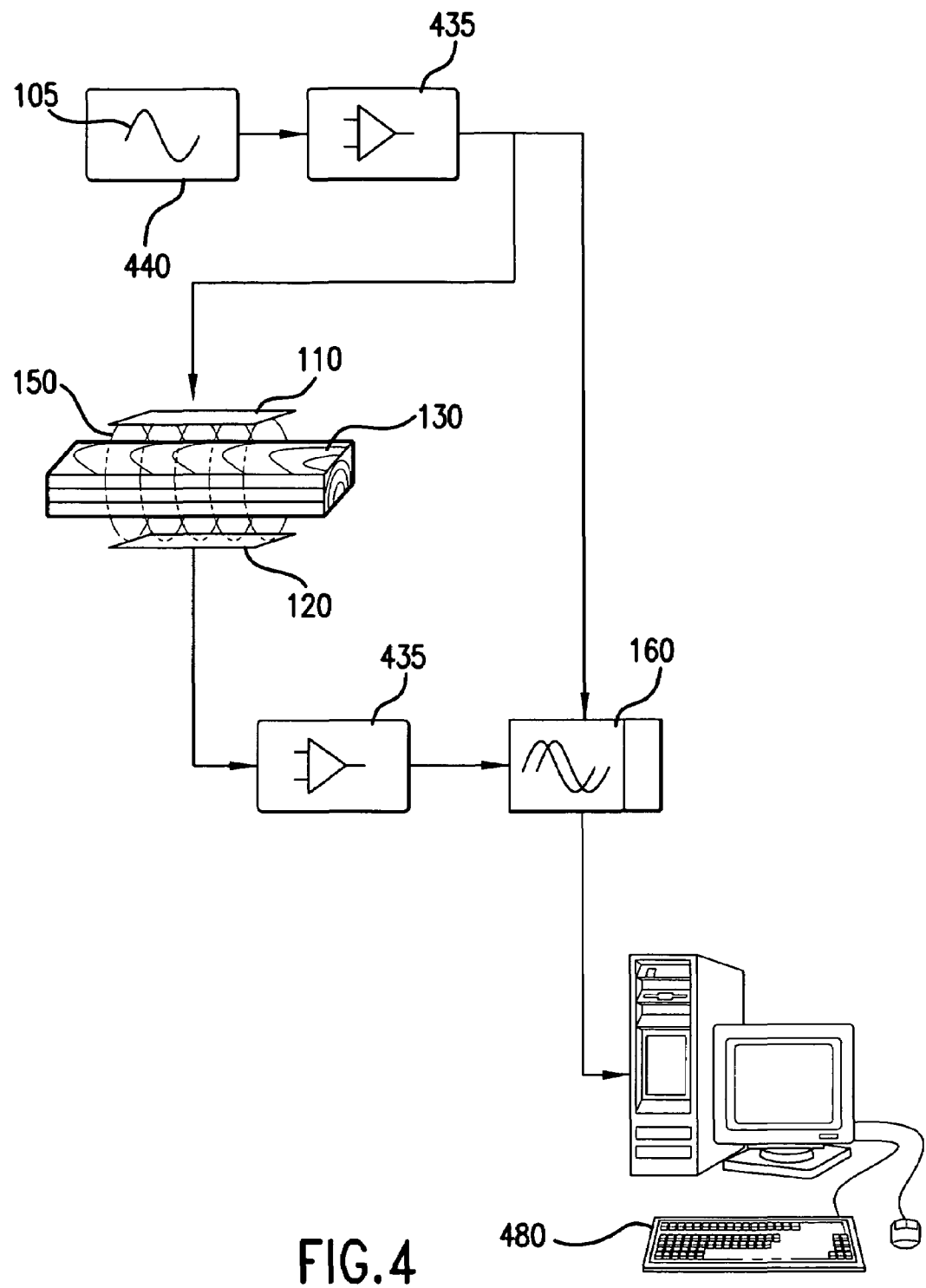
FIG. 4 displays a diagram of another exemplary embodiment of the MDD.

FIG. 4 illustrates a preferred embodiment of the MDD apparatus. The means for generating a radio frequency signal or other signal 105 is a signal generator 440. An amplifier 435 can be added to amplify the radio frequency signal or other signal 105 generated by the signal generator 440. The pair of electrodes 110 and 120 are shown with the electric field 150. Another amplifier 435 can be added to amplify the radio frequency signal or other signal 105 after it passes between the one or more pairs of electrodes 110 and 120, and before it is passed to the means for measuring the radio frequency signal or other signal 160. The means for measuring the signal strength and phase shift of the radio frequency signal or other signal, or amplitude measuring and phase comparing device 160 can be an oscilloscope 460. In this case the amplitude measuring and phase comparison is done by one device, although these measurements may each be performed by separate devices. While an oscilloscope converts analog-to-digital values automatically, other devices may not have this feature. In this case an analog to digital converter is required to convert the analog signals. The means 180 for comparing the measured radio frequency signal or other signal to predetermined values is a computer 480, which stores the signal strength and phase shift information.

FIG. 5 is a flowchart illustrating an exemplary process for determining the moisture content and/or density of any dielectric material. In step 505, the signal is generated by a signal generator 440 and transmitted to the amplifier 435. In step 510, the radio frequency signal or other signal 105 is amplified by an amplifier 435 and then transmitted to the electrodes 110 and 120. (In an exemplary embodiment the radio frequency signal or other signal is amplified. However, the amplifier 435 and amplification step 510 may be eliminated.) In step 515, the radio frequency signal or other signal 105 is applied to the transmitting electrode 110, creating an electric field 150 sensed by the receiving electrode 120.

In step 520, the radio frequency signal or other signal 105 is amplified by an amplifier 435 and then transmitted to the oscilloscope 460. (In an exemplary embodiment the radio frequency signal or other signal is amplified. However, the amplifier 435 and amplification step 520 may be eliminated.)

In step 525, the sensed radio frequency signal or other signal 150 from the receiving electrode 120 is input to the oscilloscope 460. Although the oscilloscope 460 is used in an exemplary embodiment, the radio frequency signal or other signal 105 sensed by the receiving electrode may be analyzed for amplitude and phase shift response by any device capable of measuring amplitude and of comparing the phase shift caused by interaction of the wood with the radio frequency signal or other signal. In an alternative embodiment, a spectrum analyzer, or any other competent device may be employed. A dedicated device with the single function of comparing phase shift caused by material wood interaction with the radio frequency signal or other signal will likely be the least-cost solution to the phase shift measurement.

In step 530, the computer 480 stores the digitally described signal strength and phase shift information and compares signal strength and phase shift to predetermined values to obtain estimates of moisture content and/or density.

FIG. 6 is a flowchart illustrating an exemplary process for step 530 of FIG. 5. In step 605, predetermined values needed to estimate the moisture content and density are developed. While in the exemplary embodiment provided below, the MDD used regression equations to estimate moisture content and density, such regression equations may not be required. Threshold values, physical constants, or any other values may be applied to correlate predetermined signal strength and phase shift values that will allow correlation of measured moisture content and density values to moisture content and density. Such values may be obtained by empirical observation or by theoretical analysis based on known physical relationships of the dielectric material. In step 610, phase shift and signal strength values are measured and entered into the computer 480. In step 615, the measured phase shift and signal strength values are compared to the predetermined values to determine the moisture content and/or density estimates.

Figure 7:
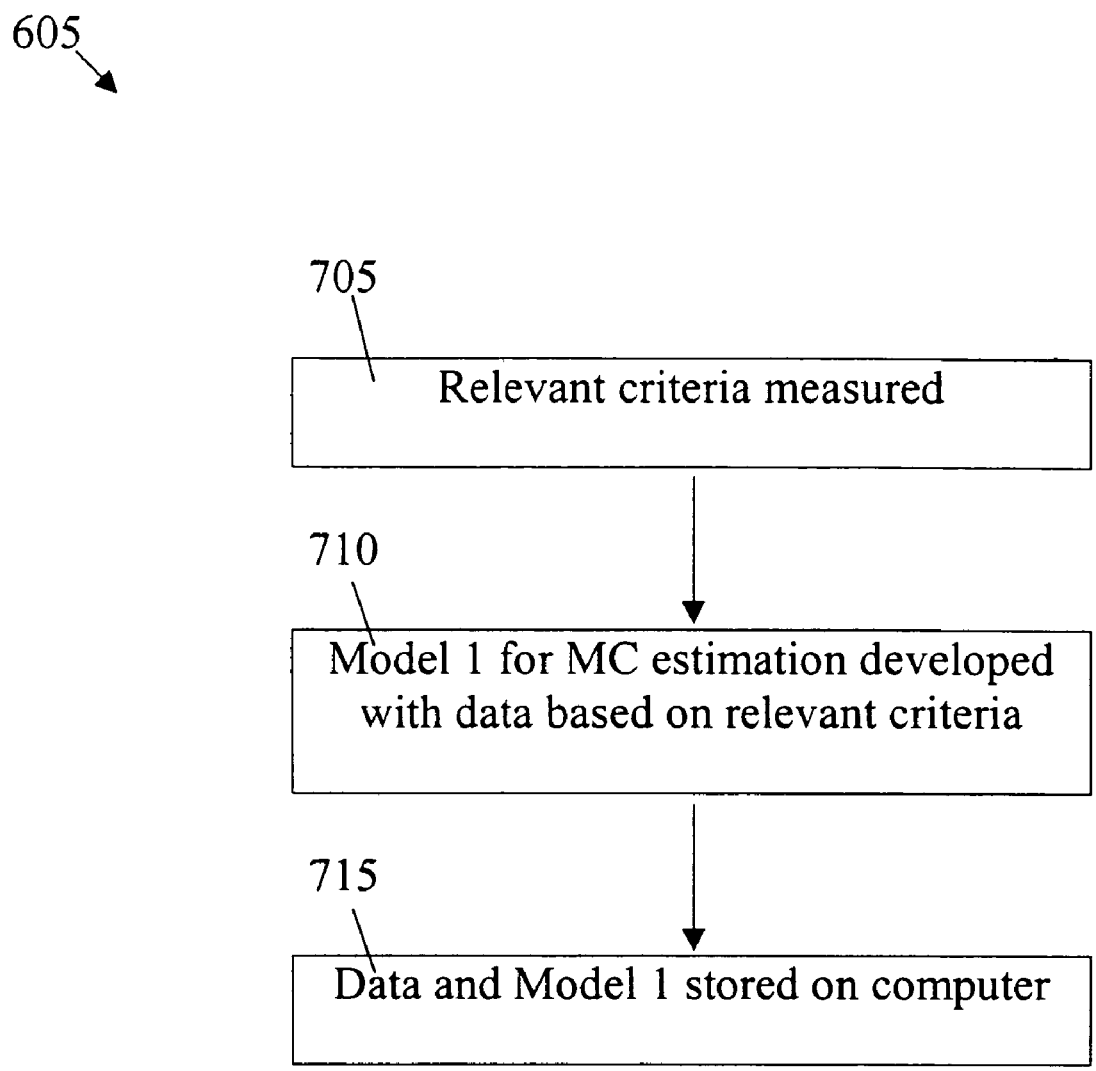
FIG. 7 is a flowchart illustrating an exemplary process for step 605 of FIG. 6.

FIG. 7 is a flowchart illustrating an exemplary process for step 605 of FIG. 6. In step 705, relevant criteria, including phase shift and signal strength, are measured using a known moisture content. For example, the MDD can measure the observed phase shift and signal strength values of each species of solid wood, the range of specific gravity values each species may exhibit, and all moisture content values the wood may exhibit. Plate material, size, shape, distance from wood surface, signal strength and frequencies employed are made to be identical to those to be applied by the device in practice. In step 710, regression equation model 1 is developed using the relevant criteria. In the example for wood, the regression equation is developed using this criteria for each species of wood and for the range of moisture content. In step 715, data and the regression equation model 1 is stored on the computer 480.

To illustrate how FIG. 7 can be applied in an exemplary embodiment, we will use the example of how the database information is compiled for the southern yellow pine lumber. In step 705, green lumber is selected from a sawmill with an attempt to sample as wide a specific gravity range as possible. Prior to drying, the green lumber is placed between the electrodes 110 and 120 to determine the influence of the moisture content and specific gravity of each piece on the signal strength and phase shift of the radio frequency signal or other signal 105. The lumber specimens are dried and periodically removed from the oven and weighed and scanned by the MDD. The periodic removals are of such a length to allow approximate reduction in moisture content of about 2 percent between MDD scanning. Frequencies applied are 0.25, 0.50, 1.0, 1.5, 2.0, 2.5, 3.0, 3.5, 4.0, 4.5 and 5.0 MHz. Initial applied voltage is 75 volts and radio frequency amplifier output power level is 10 watts. Electrode plate material is stainless steel of rectangular 3.0 inch by 9.0 inch in dimension. Plate thickness is 0.0625-inch. The lumber is to be slowly dried in an oven at 150° F.

In step 710, the regression equation Model 1 coefficients are estimated based on the data explained above, for the described variables of the MDD. The estimated regression equation Model 1 coefficients are employed to predict moisture content. In step 715, the resulting data and regression equation Model 1 are stored on the computer 480.

FIG. 8 is a flowchart illustrating an exemplary process for step 615 of FIG. 6. In step 805, regression equation Model 1 coefficients are used to calculate moisture content estimates. In step 810, a restricted moisture content range is identified about the moisture content estimates. In step 815, a reduced data set corresponding to the moisture content values with the restricted moisture content range is segregated from the total data. In step 820, a regression equation Model 2 is estimated based on the reduced data set. In step 825, the regression equation Model 2 coefficients are used to calculate specific gravity estimates based on measured values.

The following example illustrates how FIG. 8 can be applied in an exemplary embodiment. In step 805, the entered data used regression equation Model 1 coefficients to calculate an estimated moisture content of 80 percent. In step 810, a reduced set of moisture content data defined by a ±5 percent range about the 80 percent moisture content estimate is identified. In step 815, the data corresponding to the moisture content values in the reduced data set is segregated from the total data set. In step 820, The $R^2$ value for the regression equation Model 2 is estimated to be 0.99. In step 825, the regression equation Model 2 coefficients are used to calculate a specific gravity estimate based on actual measured values.

Model 1

$$MC = \mu + F + D + D^2 + PS + PS^2 + \epsilon$$

Where:
MC=estimated moisture content for loblolly pine lumber
μ=mean moisture content for loblolly pine lumber
F=applied frequency or frequencies (for this regression, data for eleven frequencies were analyzed)
D=dielectric constant (uses signal strength measured in volts)
PS=phase shift
ϵ=error term Model 2

$$SG_{mcr} = \mu + F + D + D^2 + PS + PS^2 + \epsilon$$

Where:
$SG_{mcr}$=specific gravity for loblolly pine lumber where $_{mcr}$ indicates a segregated data set corresponding to a restricted moisture content range identified about the moisture content value estimated by regression equation Model 1
μ=mean specific gravity for loblolly pine lumber other variables are as previously defined in Model 1.

What is claimed is:

1. An apparatus for estimating moisture content and density of a dielectric material, comprising:
   a generator for generating a signal;
   at least one pair of electrodes for transmitting and receiving said signal through said dielectric material;
   a circuit for measuring signal strength and/or phase shift of said signal caused by interaction of said signal with said dielectric material; and
   a micro-processor for utilizing said measured signal strength and/or phase shift of said signal to estimate moisture content and density.

2. The apparatus of claim 1, further comprising:
   at least one amplifier for amplifying said signal.

3. The apparatus of claim 2, wherein the at least one amplifier is added after the generator, and before the at least one pair of electrodes.

4. The apparatus of claim 2, wherein the at least one amplifier is added after the at least one pair of electrodes, and before the circuit.

5. The apparatus of claim 1, wherein the circuit is an oscilloscope.

6. The apparatus of claim 1, wherein the micro-processor compares predetermined values of signal strength and/or phase shift to said measured values of said signal strength and/or phase shift to estimate the moisture content and density.

7. The apparatus of claim 1, wherein the micro-processor determines threshold values based on predetermined values of signal strength and/or phase shift, and compares the threshold values to said measured values of said signal strength and/or phase shift to estimate the moisture content and density.

8. The apparatus of claim 1, wherein the micro-processor uses a regression equation to estimate the moisture content and density, the regression equation utilizing the measured signal strength and/or phase shift.

9. A method for estimating moisture content and density of a dielectric material, comprising:
   generating a signal;
   applying said signal to at least one pair of electrodes for transmitting and receiving said signal through said dielectric material;
   measuring signal strength and/or phase shift of said signal caused by interaction of said signal with said dielectric material; and
   utilizing said measured signal strength and/or phase shift of said signal to estimate moisture content and density.

10. The method of claim 9, wherein the electrodes are adjacent electrodes.

11. The method of claim 9, wherein the electrodes are opposed electrodes.

12. The method of claim 9, further comprising: amplifying said signal.

13. The method of claim 12, wherein said signal is amplified after generating said signal, and before applying said signal to the at least one pair of electrodes.

14. The method of claim 12, wherein said signal is amplified after the at least one pair of electrodes, and before the circuit.

15. The method of claim 9, wherein the step of utilizing said measured signal strength and/or phase shift of said signal to estimate moisture content and density comprises:
   developing predetermined values of said signal strength and/or phase shift for said dielectric material; and
   comparing said predetermined values of signal strength and/or phase shift to said measured values of said signal strength and/or phase shift to estimate moisture content and density.

16. The method of claim 9, wherein the step of utilizing said measured signal strength and/or phase shift of said signal to estimate moisture content and density comprises:
   determining threshold values based on predetermined values of signal strength and/or phase shift, and comparing the threshold values to said measured values of said signal strength and/or phase shift to estimate moisture content and density.

17. The method of claim 9, wherein the step of utilizing said measured signal strength and/or phase shift of said signal to estimate moisture content and density comprises:
   utilizing a regression equation to estimate the moisture content and density, the regression equation utilizing the measured signal strength and/or phase shift.

18. The method of claim 9, wherein the step of utilizing said measured signal strength and/or phase shift of said signal to estimate the at least one unknown dielectric constant in addition to moisture content comprises:
   utilizing a regression equation to estimate the at least one unknown dielectric constant in addition to moisture content, the regression equation utilizing the measured signal strength and/or phase shift.

19. An apparatus for estimating at least one unknown dielectric material characteristic in addition to moisture content, comprising:
   a generator for generating a signal;
   at least one pair of electrodes for transmitting and receiving said signal through a dielectric material;
   a circuit for measuring signal strength and/or phase shift of said signal based on interaction of said signal with said dielectric material; and
   a micro-processor for estimating at least one unknown dielectric material characteristic in addition to moisture content utilizing the measured signal strength and/or phase shift.

20. The apparatus of claim 19, wherein the unknown dielectric material characteristic is at least one of:
   an anomaly;

a wood type;
density; and
a material type.

21. The apparatus of claim 19, further comprising:
at least one amplifier for amplifying said signal.

22. The apparatus of claim 21, wherein the at least one amplifier is added after the generator, and before the at least one pair of electrodes.

23. The apparatus of claim 21, wherein the at least one amplifier is added after the at least one pair of electrodes, and before the circuit.

24. The apparatus of claim 19, wherein the circuit is an oscilloscope.

25. The apparatus of claim 19, wherein the dielectric material is at least one of:
wood;
a wood-based material;
a wood composite material;
an agricultural product;
a food product;
plastic; and
rubber.

26. The apparatus of claim 19, wherein the micro-processor compares predetermined values of signal strength and/or phase shift to said measured values of said signal strength and/or phase shift to estimate the at least one unknown dielectric constant in addition to moisture content.

27. The apparatus of claim 19, wherein the micro-processor determines threshold values based on predetermined values of signal strength and/or phase shift, and compares the threshold values to said measured values of said signal strength and/or phase shift to estimate the at least one unknown dielectric constant in addition to moisture content.

28. The apparatus of claim 19, wherein the micro-processor uses a regression equation to estimate the at least one unknown dielectric constant in addition to moisture content, the regression equation utilizing the measured signal strength and/or phase shift.

29. A method for estimating at least one unknown dielectric material characteristic in addition to moisture content, comprising:
generating a signal;
transmitting and receiving said signal through a dielectric material;
measuring signal strength and/or phase shift of said signal based on interaction of said signal with said dielectric material; and
utilizing said measured signal strength and/or phase shift to estimate at least one unknown dielectric material characteristic in addition to moisture content.

30. The method of claim 29, wherein the electrodes are adjacent electrodes.

31. The method of claim 29, wherein the electrodes are opposed electrodes.

32. The apparatus of claim 29, wherein the unknown dielectric material characteristic is at least one of:
an anomaly;
a wood type;
density; and
a material type.

33. The method of claim 29, further comprising:
amplifying said signal.

34. The method of claim 33, wherein said signal is amplified after generating said signal, and before applying said signal to the at least one pair of electrodes.

35. The method of claim 33, wherein said signal is amplified after the at least one pair of electrodes, and before the circuit.

36. The method of claim 29, wherein the dielectric material is at least one of:
wood;
a wood-based material;
a wood composite material;
an agricultural product;
a food product;
plastic; and
rubber.

37. The method of claim 29, wherein the step of utilizing said measured signal strength and/or phase shift of said signal to estimate the at least one unknown dielectric constant in addition to moisture content comprises:
developing predetermined values of said signal strength and/or phase shift for said dielectric material; and
comparing said predetermined values of signal strength and/or phase shift to said measured values of said signal strength and/or phase shift to estimate the at least one unknown dielectric constant in addition to moisture content.

38. The method of claim 29, wherein the step of utilizing said measured signal strength and/or phase shift of said signal to estimate the at least one unknown dielectric constant in addition to moisture content comprises:
determining threshold values based on predetermined values of signal strength and/or phase shift, and comparing the threshold values to said measured values of said signal strength and/or phase shift to estimate the at least one unknown dielectric constant in addition to moisture content.

39. An apparatus for estimating at least one of moisture content and density of a dielectric material, comprising:
a generator for generating a signal;
at least one pair of electrodes for transmitting and receiving said signal through said dielectric material;
a circuit for measuring signal strength and/or phase shift of said signal caused by interaction of said signal with said dielectric material; and
a micro-processor for estimating moisture content and density of said dielectric material, using said measured signal strength and/or phase shift of said signal, wherein the predetermined threshold values include signal strength and phase shift for a range of densities and a range of moisture contents for each density in the range of densities.

40. The apparatus of claim 39, further comprising: at least one amplifier for amplifying said signal.

41. The apparatus of claim 40, wherein the at least one amplifier is added after the generator, and before the at least one pair of electrodes.

42. The apparatus of claim 40, wherein the at least one amplifier is added after the at least one pair of electrodes, and before the circuit.

43. The apparatus of claim 39, wherein the circuit is an oscilloscope.

44. A method for estimating at least one of moisture content and density of a dielectric material, comprising;
generating a signal;
applying said signal to at least one pair of electrodes for transmitting and receiving said signal through said dielectric material;
measuring signal strength and/or phase shift of said signal caused by interaction of said signal with said dielectric material; and utilizing said measured signal strength and/or phase shift of said signal to estimate at least one of moisture content and density using predetermined threshold values which include signal strength and phase shift for a range of densities and a range of moisture contents for each density in the range of densities.

45. The method of claim 44, wherein the electrodes are adjacent electrodes.

46. The method of claim 44, wherein the electrodes are opposing electrodes.

47. The method of claim 44, further comprising: amplifying said signal.

48. The method of claim 47, wherein said signal is amplified after generating said signal, and before applying said signal to the at least one pair of electrodes.

49. The method of claim 47, wherein said signal is amplified after the at least one pair of electrodes, and before the circuit.

50. The method of claim 46, further comprising:
developing predetermined threshold values of said signal strength and/or phase shift for said dielectric material.

* * * * *